US010267798B2

(12) United States Patent
Kurreck et al.

(10) Patent No.: US 10,267,798 B2
(45) Date of Patent: Apr. 23, 2019

(54) METHOD FOR DETECTING PROTEINS BY MEANS OF APTAMERS

(71) Applicant: Technische Universität Berlin, Berlin (DE)

(72) Inventors: Jens Kurreck, Berlin (DE); Anke Wagner, Berlin (DE); Viola Röhrs, Berlin (DE)

(73) Assignee: TECHNISCHE UNIVERSITÄT BERLIN, Berlin (DE)

( * ) Notice: Subject to any disclaimer, the term of this patent is extended or adjusted under 35 U.S.C. 154(b) by 320 days.

(21) Appl. No.: 15/042,732

(22) Filed: Feb. 12, 2016

(65) Prior Publication Data

US 2016/0238602 A1 Aug. 18, 2016

(30) Foreign Application Priority Data

Feb. 13, 2015 (EP) .................... 15075007

(51) Int. Cl.
| | | |
|---|---|---|
| *G01N 31/00* | (2006.01) | |
| *G01N 33/53* | (2006.01) | |
| *G01N 33/573* | (2006.01) | |
| *G01N 33/68* | (2006.01) | |

(52) U.S. Cl.
CPC ....... *G01N 33/573* (2013.01); *G01N 33/5306* (2013.01); *G01N 33/68* (2013.01); *G01N 33/6803* (2013.01); *G01N 2333/36* (2013.01); *G01N 2333/974* (2013.01)

(58) Field of Classification Search
None
See application file for complete search history.

(56) References Cited

U.S. PATENT DOCUMENTS

| 7,371,833 B1 | 5/2008 | Weiss |
| 2014/0148356 A1 | 5/2014 | Li et al. |

FOREIGN PATENT DOCUMENTS

| WO | 00/73501 A2 | 12/2000 | |
| WO | 2011/060557 A1 | 5/2011 | |
| WO | WO 2011/060557 | * 5/2011 | ............... C12Q 1/68 |

OTHER PUBLICATIONS

Wang et al. (Anal. Bioanal Chem. Sep. 2011, 401(4) pp. 1309-1318).*
Pultar et al. (Biosensors and Bioelectronics, 24, 2009, pp. 1456-1461).*
Shin et al., "An alternative to Western blot analysis using RNA aptamer-functionalized quantum dots": Bioorganic & Medicinal Chemistry Letters; No. 20, (2010) pp. 3322-3325.
Rhie et al,; "Characterization of 2-fluoro-RNA Aptamers That Bind Preferentially to Disease-associated Conformations of Prion Protein and Inhibit Conversion"; vol. 278, No. 41, Oct. 10, 2003, pp. 39697-39705.
Moreno et al.; "Selection of aptamers against KMP-11 using colloidal gold during the SELEX process", Biochemical and Biophysical Research Communications, vol. 308; (2003), pp. 214-218.
XP055203732—"Best Practices: Western Bolt"; Base Pair Biotechnologies, Aug. 12, 2014.
Song et al., "Aptamers and Their Biological Applications"; Sensors, No. 12, 2012, pp. 612-631.
European Search Report dated Jul. 21, 2015.

* cited by examiner

*Primary Examiner* — Lisa V Cook
(74) *Attorney, Agent, or Firm* — Norris McLaughlin, PA (57) ABSTRACT

A method is provided for an in vitro detection of a first protein in a sample, including the steps of: a) separating the sample by a native separation method; b) transferring the separated sample onto a membrane; c) contacting the membrane with an aptamer which specifically binds to the first protein; and d) detecting the first protein by detecting the aptamer bound to the first protein.

15 Claims, 10 Drawing Sheets

Specification includes a Sequence Listing.

METHOD FOR DETECTING PROTEINS BY MEANS OF APTAMERS

The invention relates to a method for detecting proteins by means of aptamers.

The prior art knows various methodological approaches to detect proteins. Methods, such as ELISA (Enzyme Linked Immunosorbent Assay), Dot Blot or Western Blot, are commonly used, which are all based on the specific detection of proteins by means of antibodies. The use of antibodies, however, entails a diversity of disadvantages: The production of antibodies is generally a complicated, time-consuming and costly process. To manufacture polyclonal or monoclonal antibodies, it is also necessary to use animals directly for immunisation, or to obtain cells from them in order to apply the hybridom technology.

It is known that aptamers can serve as substitutes for antibodies in many applications. The use of aptamers instead of antibodies has a number of benefits, the aptamers are e.g. produced in vitro, so that no animal experiments or animal cell cultures are required in contrast to the classic antibody production. As aptamers are made by way of chemical synthesis, there are also no variations among the individual batches produced. Furthermore, the in vitro selection process makes it possible to produce aptamers against target molecules which are cytotoxic or have a low immunogenicity.

Like antibodies, aptamers can be modified by means of marker or reporter molecules so as to be detected in the most various methodological applications. Detection methods based on biotinylated aptamers, radioactively or fluorescently labelled aptamers or aptamer-fusion nanoparticles are already known in the prior art.

A major challenge for establishing aptamer-based detection methods, especially in blot applications, is to optimise the specificity. For example, the use of nanoparticles usually creates a highly unspecific background, which probably is due to the fact that nanoparticles can also interact with proteins. The detection of biotinylated aptamers by means of streptavidin-HRP can result in unspecific signals, too, in particular in heterogeneous protein mixtures because streptavidin strongly interacts with biotin and thus biotinylated proteins are also detected.

It is the purpose of the present invention to reduce or avoid one or several disadvantages according to the prior art. Especially, it is a purpose of the present invention to provide a method which enables a specific detection of one protein in one sample.

A first aspect of the present invention is to provide a method for an in vitro detection of a first protein in a sample, comprising the steps of: a) separating the sample by means of a native separation method; b) transferring the separated sample onto a membrane; c) contacting the membrane with an aptamer which specifically binds to the first protein; and d) detecting the first protein by means of detection of the aptamer bound to the first protein. Surprisingly, it was found that an improved detection of proteins by means of aptamers is possible after separating a sample using a native separation method.

A second aspect of the present invention is to provide a method for an in vitro detection of a first protein in a sample, comprising the steps of: a) separating the sample by means of a native separation method; b) transferring the separated sample onto a membrane; c) contacting the membrane with an aptamer which specifically binds to the first protein, wherein the contacting takes place at a temperature of $\geq 30°$ C.; and d) detecting the first protein by means of detection of the aptamer bound to the first protein.

Surprisingly, it was found that a more specific detection of proteins in a sample becomes possible if the membrane is brought in contact with an aptamer at a temperature of $\geq 30°$ C.

Unless the following context clearly indicates otherwise, the use of singular or plural forms always comprises both the singular and the plural.

The method according to the invention relates to a method for an in vitro detection of a protein in one sample. It is possible by means of the method according to the invention to make both a qualitative assessment on the presence or absence of the protein in the sample, and a quantitative or semi-quantitative assessment regarding the amount of protein within this sample. The first protein to be identified in a sample can be a protein of any type or origin. For example, the first protein can be a natural protein from an animal, a plant, bacterium or a similar source, or it can be of synthetic origin. The first protein can be a polypeptide, oligopeptide or a peptide. It can be bound to other molecules or structures, such as a membrane protein, but it can also be a soluble protein, such as a hormone. For instance, the first protein can also have enzymatic or toxic properties. The first protein can include modifications, such as phosphorylations, hydroxylations, methylations, glycolysations or the like. Preferably, the first protein is a human protein, more preferably a soluble protein, and most preferably α-thrombin.

The term "sample" denotes a composition to be tested that can be used for the ex vivo or in vitro assay. The sample is preferably a biological or medical material, namely a material obtained from an organism, from parts of an organism or from cells. The material can undergo further treatment steps before it is used as a sample in the method according to the invention, e.g. in order to put the material into a condition in which it is particularly suited as a sample for the method according to the invention. To prepare the sample, methods can be used which are known to those skilled in the art.

The sample preferably comprises a protein-containing mixture. The protein-containing mixture can include one or a plurality of proteins as well as other components. The protein-containing mixture can be obtained from a cell culture suspension or a cell culture supernatant, or comprise a cell culture suspension or a cell culture supernatant. The protein-containing mixture can also be obtained from a tissue sample to be tested or comprise a tissue sample. Preferably, it is a tissue sample from a test person, wherein the test person can be an animal, preferably a mammal, more preferably a human. Furthermore, the protein-containing mixture can be obtained from a body fluid or comprise a body fluid. "Body fluid" can be any fluid of the body, e.g. blood, plasma, serum, synovial fluid, urine, stool, interstitial fluid, lymph, saliva, sweat, spinal fluid, lacrimal fluid, etc.

The detection method according to the present invention is carried out in vitro. "In vitro" means any environment which is not within a living organism, e.g. a human or animal body. The in vitro detection method according to the invention does explicitly not comprise any method carried out on the human or animal body.

In the method according to the invention, the sample is separated in a first step a) by means of a native separation method. The term "separation method" means in the context of the present invention a method that takes advantage of the different physical and chemical properties of components mixed with each other in order to separate them from each other. The individual components can be separated e.g. based on their different sizes, charges, solubility or isoelectric points. Suitable methods to separate samples containing at least one first protein are known to those skilled in the art. The term "native" in the expression "native separation method" means that the natural protein folding of the protein to be detected is essentially maintained during the separation method, i.e. in most cases no or at least no complete denaturation of the protein takes place, so that its native secondary, tertiary or quarternary structures remain essentially unaffected. Preferably, the native separation method is an electrophoretic separation, preferably a gel electrophoresis, such as the native polyacrylamide gel electrophoresis (PAGE) or the isoelectric focusing (IEF). The native separation method is especially characterised in that an SDS concentration of 0% to 0.2 SDS, preferably of 0.01% to 0.15% SDS, more preferably of 0.1% SDS is used.

In the method according to the invention the sample is separated in a first step a) by means of a separation method. The term "separation method" means in the context of the present invention a method that takes advantage of the different physical and chemical properties of components mixed with each other in order to separate them from each other. The individual components can be separated e.g. based on their different sizes, charges, solubility or isoelectric points. Suitable methods to separate samples containing at least one first protein are known to those skilled in the art. The separation method can be applied both under native and under denaturating conditions. In the method according to the invention the sample is preferably separated by means of a native separation method. The term "native" in the expression "native separation method" means that the natural protein folding of the protein to be detected is essentially maintained during the separation method, i.e. in most cases no or at least no complete denaturation of the protein takes place, so that its native secondary, tertiary or quarternary structures remain essentially unaffected. Preferably, the native separation method is an electrophoretic separation, preferably a gel electrophoresis, such as the native polyacrylamide gel electrophoresis (PAGE) or the isoelectric focusing (IEF). The native separation method is especially characterised in that an SDS concentration of 0% to 0.2% SDS, preferably of 0.01% to 0.15% SDS, more preferably of 0.1% SDS is used.

In a next step of the method according to the invention a transfer of the separated sample onto a membrane is performed (step b). After the transfer onto the membrane, the membrane can be optionally blocked such that free unspecific binding sites on the membrane are made inaccessible for a binding. The membrane can be blocked by means of e.g. powdered milk, albumin, such as bovine serum albumin (BSA), gelatin or the like. Suitable conditions under which the transfer or the blocking of the membrane can be carried out are known to those skilled in the art.

In the following step c) of the method according to the invention, the membrane is brought in contact with an aptamer which specifically binds to the first protein.

"Aptamer" in the spirit of the method according to the invention means a single-stranded oligonucleotide of a nucleic acid molecule, such as a ribonucleic acid (RNA) or a single-stranded desoxyribonucleic acid (ssDNA). If the aptamer comprises a ribonucleic acid, it can be called an RNA aptamer. If it comprises, however, a desoxyribonucleic acid, it can be called a DNA aptamer.

Due to its special three-dimensional structure an aptamer binds specifically and with a high affinity to its target molecule, e.g. to a protein in a sample. The term "specific" or "specific binding" means that under the selected conditions the aptamer can preferably bind selectively to the target molecule to be detected.

Aptamers include or consist of a sequence of nucleic acid molecules made of individual nucleotides. Nucleotides consist of three components, namely phosphates, one sugar and a nucleobase. The term "nucleotides" herein refers both to ribonucleotides and to desoxyribonucleotides. According to the general one-letter codes for nucleobases "A" stands for adenine, "C" for cytosine, "G" for guanine, "T" for thymine and "U" for uracil, wherein the nucleobase thymine in RNA aptamers is substituted by uracil.

The aptamer is specifically preferred for one first protein.

Contacting the membrane with the aptamer preferably includes a liquid environment and is carried out over a period of time allowing for the specific binding between the first protein and the corresponding aptamer. This period of time is preferably longer than 30 seconds, more preferably longer than 5 minutes, and most preferably 5 minutes to 48 hours. An incubation period of 1 hour is especially preferred.

Contacting the membrane with the aptamer in step c) of the method according to the invention preferably occurs at a temperature of room temperature. "Room temperature" means a temperature ranging from 18° C. to 25° C. The incubation of the membrane at a higher temperature than the room temperature can surprisingly have an advantageous effect on the specificity of the protein detection. Thus, an increased incubation temperature shows a considerably reduced background signal of the membrane as such and also lower signals of unspecific bindings. "Increased" in the sense of a temperature higher than room temperature means that an incubation temperature above 25° C. is chosen. Preferably, the membrane is contacted with the aptamer in step c) at a temperature of >25° C. Preferably, the contacting of the membrane with the aptamer in step c) takes place at a temperature of ≥30° C., preferably at 30° C. to 70° C., more preferably at 40° C. to 60° C., particularly preferably at 40° C. to 50° C. Most preferably the contacting of the membrane is performed at a temperature of 50° C.

Irrespective of the type of separation method in step a) the contacting of the membrane with the aptamer in step c) of the method according to the invention preferably takes place at a temperature ≥30° C. Surprisingly, it was found that the incubation of the membrane at a temperature higher than room temperature has an advantageous effect on the specificity of the protein detection. Thus, an increased incubation temperature of the membrane shows a considerably reduced background signal of the membrane as such and also lower signals of unspecific bindings. Preferably, the contacting takes place at a temperature of 30° C. to 70° C., more preferably at 40° C. to 60° C., particularly preferably at 40° C. to 50° C. Most preferably, the contacting of the membrane is performed at a temperature of 50° C.

In the following step d) of the method according to the invention the first protein is detected by means of detection of the aptamer which is bound to the first protein. The detection can be performed in one or a plurality of steps. After contacting the membrane with the aptamer and prior to its detection it is possible to remove those components from the test that have not bound to the first protein. This could be done through one or a plurality of washing, cleaning or isolating steps.

This detection can be direct or indirect. A direct detection of the aptamer can be carried out if the aptamer includes a modification with a labelling which can be used to directly detect the labelled aptamer. Those skilled in the art know both suitable labellings and methods by which aptamers can be modified. Preferred modifications are e.g. fluorescent labellings, radioisotope labellings, peroxidase labellings, alkaline phosphatase labellings or labellings using nanoparticles. The aptamer preferably has a fluorescent labelling, more preferably a labelling with a fluorescein, in particular with 6-carboxyflourescein. A labelling using a cyanine dye, especially Cy5, is also preferred.

Methods for directly detecting the modified aptamers are known to those skilled in the art. If the modification of the aptamer is for example a fluorescent labelling, the resulting fluorescence can be detected by exciting the fluoro-phosphor at a suitable wavelength.

The detection is preferably an enzymatic, auto-radiographic or fluorescent detection, more preferably a fluorescent detection method.

The aptamer can also be detected indirectly. For example, the indirect detection can be carried out if the aptamer includes a modification with a labelling that can be used to indirectly detect the labelled aptamer. Preferred labellings are e.g. biotin labellings or digoxigenin labellings. The indirect detection of the aptamer preferably uses an aptamer-specific antibody bound to the aptamer.

The aptamer-specific antibody can include a modification with a labelling that can be used for the further detection of the aptamer-specific antibody. Those skilled in the art know suitable labellings as well as methods by which aptamer-specific antibodies can be modified. Preferred modifications are e.g. biotin labellings, fluorescent labellings, radioisotope labellings, digoxigenin labellings, peroxidase labellings, alkaline phosphate labellings or labellings using nanoparticles.

The method according to the invention can be used to detect a first protein in a sample. The present invention also comprises a method for the additional in vitro detection of a second protein in the sample, wherein in addition to the above-described steps a) to d) for detecting a first protein the further steps i) and ii) are performed in order to detect a second protein in the sample. The sample used here is identical to the sample in which the first protein is detected by the method of the invention. Accordingly, one first and one second protein are detected in a single sample.

Following step b) of the method for detecting the first protein, the membrane is brought in contact with a binding molecule which specifically binds to the second protein (step i) to detect the second protein in the sample. Then the second protein is detected by detecting the binding molecule bound to the second protein (step ii).

Step i) of the method for detecting a second protein in the sample can be performed before, during or after step c) of the method for detecting the first protein in the sample. In any case, step i) is carried out after step b). Independent of this, step ii) for detecting the second protein in the sample can be performed before, during or after step d) of the method for detecting the first protein in the sample. The exact timing of step i) depends among other things on the type of the selected binding molecule and the chosen test conditions of the method.

The term "second protein" means a protein which is not the same protein as the first one in the individual embodiments. Correspondingly, if the first protein is e.g. an α-thrombin, the second protein can be any other protein except an α-thrombin. The second protein can also be a second epitope of the first protein. The second protein is preferably streptavidin.

In the method according to the invention the term "a binding molecule" or "binding molecules" denotes such substances which can preferably bind selectively to the second protein to be detected under the selected conditions. Those skilled in the art know suitable binding molecules and methods to make them. The binding molecules can be based on polypeptides, poly- or oligonucleic acids or the like.

The binding molecule is preferably a further aptamer. The definition of the expression a "further aptamer" corresponds to the definition of "aptamer" provided that the further aptamer in the individual embodiments does not have the same specificity as the aptamer. Therefore, if the aptamer has for example a specificity for a first protein, the further aptamer can have any other specificity except the one for the first protein. The further aptamer and the aptamer can differ from each other by their epitope specificities, sequences and/or labellings.

The further aptamer is preferred specifically for a second protein.

Similarly preferably, the binding molecule can be a polypeptide, such as a cell adhesion molecule from the integrin, cadherin, selectin groups, or members of the immunoglobulin (Ig) superfamily. The peptide is preferably an antibody, wherein it can comprise a polyclonal and a monoclonal antibody having a classic antibody structure as well as derivates or fragments derived therefrom. Such fragments are known as Fab, F(ab)$_2$, dsFv fragments, scFV fragments and single-chain antibodies. The binding molecule is preferably an antibody.

In step ii) of the method according to the invention, the second protein is detected by detecting the binding molecule which is bound to the second protein. The detection can be performed in one or a plurality of steps. After contacting the membrane with the binding molecule (step i)) and prior to its detection in step ii) it is possible to remove those components from the test that have not bound to the second protein. This could be done e.g. by means of one or a plurality of washing, cleaning or isolating steps. This detection can be direct or indirect.

A direct detection of the binding molecule can be carried out if the binding molecule includes a modification with a labelling which can be used to further detect the labelled binding molecule. Those skilled in the art know suitable labellings as well as methods by which binding molecules can be modified. Preferred modifications are e.g. biotin labellings, fluorescent labellings, radioisotope labellings, digoxigenin labellings, peroxidase labellings, alkaline phosphate labellings or labellings using nanoparticles. The binding molecule preferably has a fluorescent labelling, more preferably a labelling with a fluorescein, in particular with 6-carboxyflourescein. A labelling using a cyanine dye, especially Cy5, is also preferred.

Methods for directly detecting the modified binding molecules are known to those skilled in the art. If the binding molecule is for example modified by fluorescent labelling, the resulting fluorescence can be detected by exciting the fluoro-phosphor at a suitable wavelength. The direct detection is preferably an enzymatic, auto-radiographic or fluorescent detection, more preferably a fluorescent detection method.

The binding molecule can also be indirectly detected. The indirect detection of the binding molecule preferably uses a binding molecule-specific antibody which is bound to the binding molecule.

The binding molecule-specific antibody can include a modification with a labelling that can be used to further detect the binding molecule-specific antibody. Those skilled in the art know suitable labellings as well as methods by which binding molecule-specific antibodies can be modified. Preferred modifications are e.g. biotin labellings, fluorescent labellings, radioisotope labellings, digoxigenin labellings, peroxidase labellings, alkaline phosphate labellings or labellings using nanoparticles.

In a preferred embodiment of the present invention, the method for an in vitro detection of a first protein in a sample comprises the steps of: a) separating the sample by means of a separation method, e.g. a native separation method; b) transferring the separated sample onto a membrane; c) contacting the membrane with an aptamer which specifically binds to the first protein, wherein the contacting can take place at a temperature of 40° C. to 60° C.; and d) detecting the first protein by means of detection of the aptamer bound to the first protein, wherein the aptamer has a fluorescent labelling and the labelled aptamer is directly detected by means of a fluorescent detection method.

In another preferred embodiment, a first protein in a sample is detected by means of an aptamer and a second protein is detected in vitro by means of a further aptamer. The method according to the present invention comprises the steps of: a) separating the sample by means of a separation method, e.g. a native separation method; b) transferring the separated sample onto a membrane; c) contacting the membrane with an aptamer which specifically binds to the first protein, wherein the contacting can take place e.g. at a temperature of 40° C. to 60° C.; and contacting the membrane with a further aptamer which specifically binds to the second protein (step i)); and d) detecting the first protein by means of detection of the aptamer bound to the first protein, and detecting the second protein by means of detection of the further aptamer bound to the second protein (step ii)). Step i) can be carried out before, during or after step c) of the method. Furthermore, step ii) can be performed before, during or after step c) of the method. Both the aptamer and the further aptamer have a fluorescent labelling. The labelled aptamer and the labelled further aptamer are detected by means of a direct detection, wherein the direct detection is a fluorescent detection method.

In another preferred embodiment, a first protein in a sample is detected by means of an aptamer and a second protein is detected in vitro by means of an antibody as a binding molecule. The method according to the present invention comprises the steps of: a) separating the sample by means of a separation method, e.g. a native separation method; b) transferring the separated sample onto a membrane; c) contacting the membrane with an aptamer which specifically binds to the first protein, wherein the contacting can take place e.g. at a temperature of 40° C. to 60° C.; and contacting the membrane with an antibody which specifically binds to the second protein (step i)); and d) detecting the first protein by means of detection of the aptamer bound to the first protein, and detecting the second protein by means of detection of the antibody which is bound to the second protein (step ii)). Step i) can be carried out before, during or after step c) of the method. Furthermore, step ii) can be performed before, during or after step c) of the method.

In an especially preferred embodiment, a first protein in a sample is detected by means of an aptamer and a second protein is detected in vitro by means of an antibody as a binding molecule. The method according to the present invention comprises the steps of: a) separating the sample by means of a separation method, e.g. a native separation method; b) transferring the separated sample onto a membrane; c) contacting the membrane with an aptamer which specifically binds to the first protein, wherein the contacting can take place e.g. at a temperature of 40° C. to 60° C.; and contacting the membrane with an antibody which specifically binds to the second protein (step i)); and d) detecting the first protein by means of detection of the aptamer bound to the first protein, and detecting the second protein by means of detection of the antibody which is bound to the second protein (step ii)). Step i) can be carried out before, during or after step c) of the method. Furthermore, step ii) can be performed before, during or after step c) of the method. Both the aptamer and the antibody can have a fluorescent labelling. The labelled aptamer and the labelled antibody are detected by means of a direct detection, wherein the direct detection is a fluorescent detection method.

In another especially preferred embodiment, a first protein in a sample is detected by means of an aptamer and a second protein is detected in vitro by means of an antibody as a binding molecule. The method according to the present invention comprises the steps of: a) separating the sample by means of a separation method, e.g. a native separation method; b) transferring the separated sample to a membrane; c) contacting the membrane with an aptamer which specifically binds to the first protein, wherein the contacting can take place e.g. at a temperature of 40° C. to 60° C.; and contacting the membrane with an antibody which specifically binds to the second protein (step i)); and d) detecting the first protein by means of detection of the aptamer bound to the first protein and detecting the second protein by means of detection of the antibody which is bound to the second protein (step ii)). Step i) can be carried out before, during or after step c) of the method. Furthermore, step ii) can be performed before, during or after step c) of the method. The aptamer has a fluorescent labelling and is detected directly, preferably by means of a fluorescent labelling method. The antibody is detected indirectly using another antibody which specifically binds to the antibody (so-called binding molecule-specific antibody).

It is also possible to detect even further proteins in addition to a first and a second protein in the same sample by means of the method according to the invention.

The present invention also relates to the application of the method according to the invention for the in vitro detection of one protein in a sample.

Besides, the present invention relates to the use of the method according to the invention for the in vitro diagnosis of a disease that can be diagnosed by detecting the presence or absence of a protein in a sample.

The invention is explained in more detail using embodiments and the corresponding figures.

FIGURES

FIGS. 3A-3D Specificity increase of the aptamer blot. The influence of the aptamer incubation at 50° C. was compared with an experimental design that was incubated in parallel at room temperature. (FIG. 3A) 1 µg and 2 µg of human α-thrombin was mixed with HeLa extract and analysed by means of an aptamer blot. The influence of 0.6M NaCl or 6M urea was determined in comparison with an aptamer incubation temperature of 50° C. and with the untreated initial solution. (FIG. 3B) Streptavidin was expressed as a fusion protein with the maltose-binding protein (MBP-Str) in E. coli. A cell extract of the expression strain without an MBP-Str-producing plasmid was tested as a control.

EXAMPLES

Figure 1A:
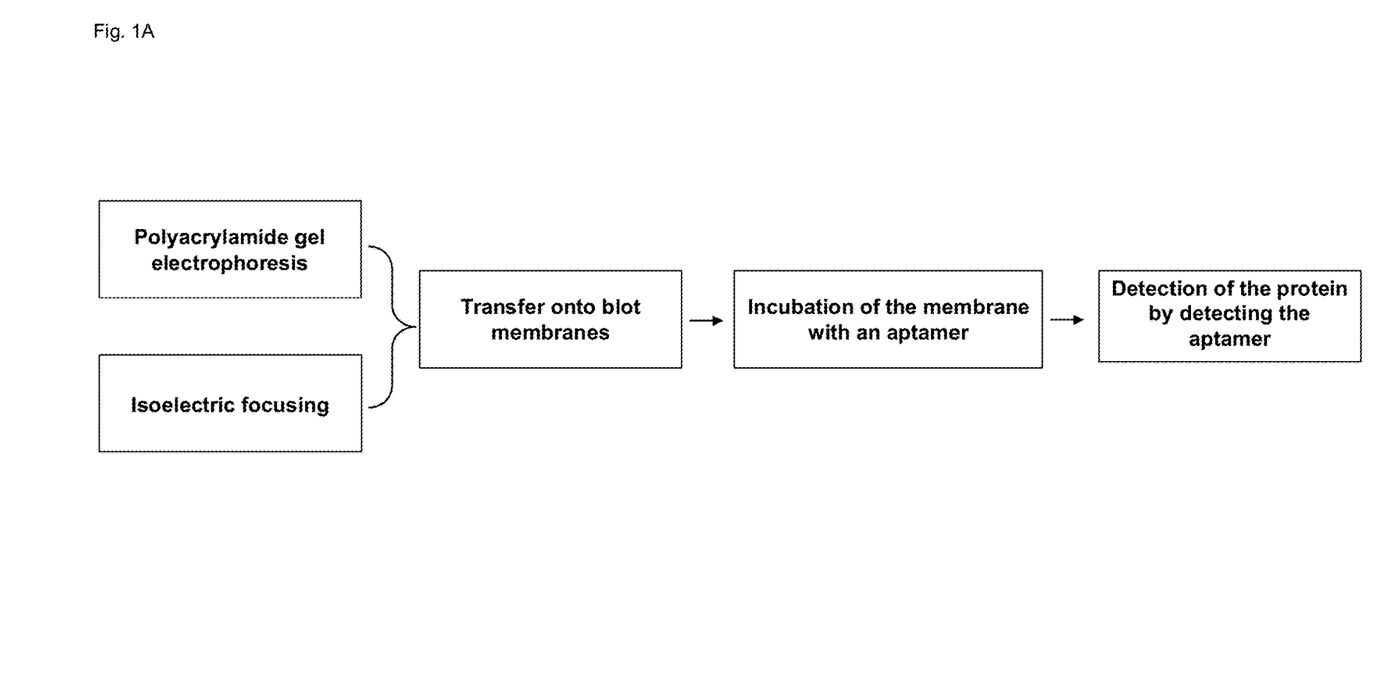
FIGS. 1A and 1B Protocols for detecting proteins in the aptamer blot (FIG. 1A) or in the combined aptamer and western blots (FIG. 1B).
Figure 1B:
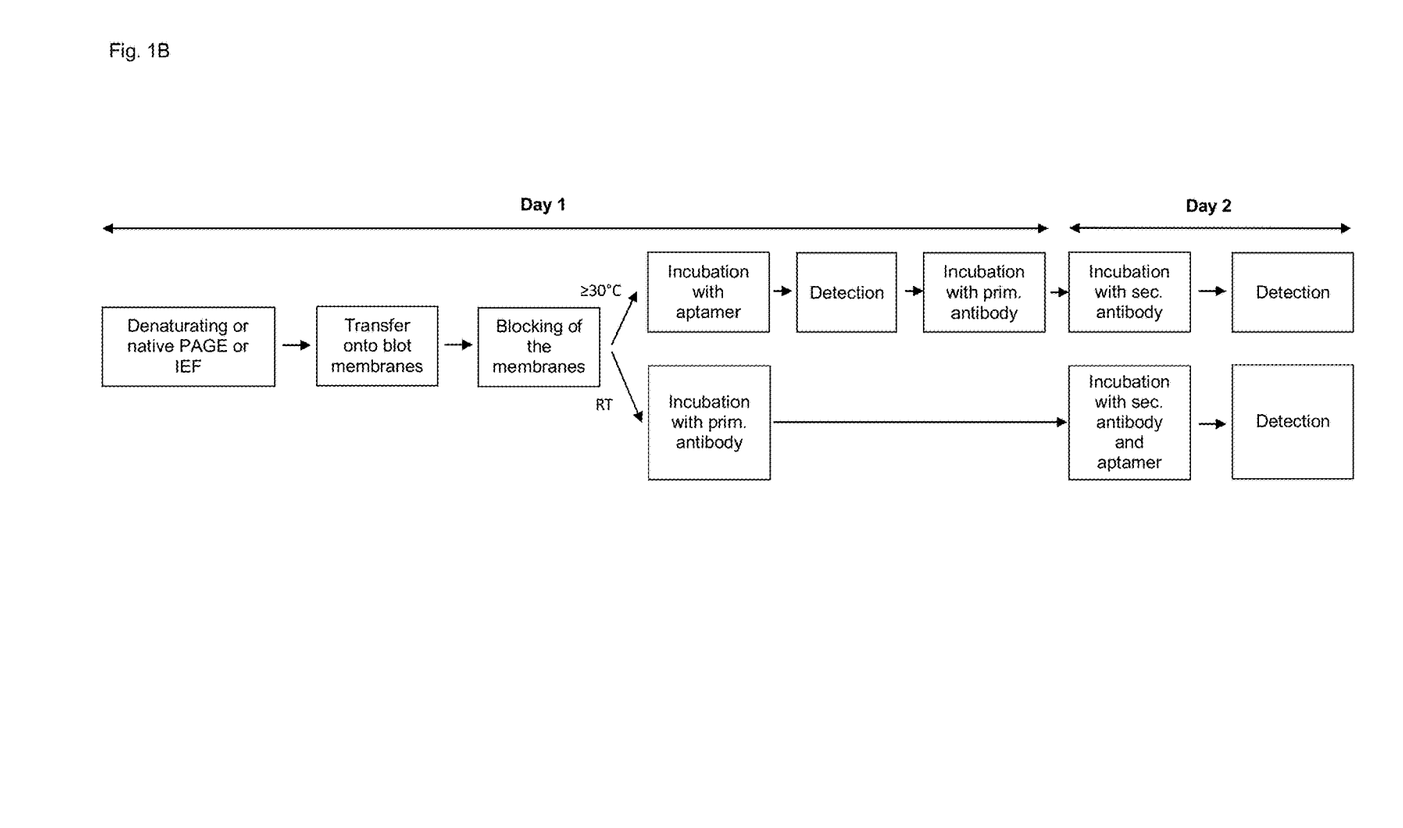

The method according to the invention serves the detection of proteins in protein-containing mixtures, such as cell extracts, tissue samples or the like, by means of specific aptamers. The protein detection protocol is shown in FIGS. 1A and 1B.

The aptamers used in the method contain or consist of a nucleic acid sequence of 15 nucleotides having the SEQ ID No. 1, or of 40 nucleotides having the SEQ ID No. 2. The 15-mer: GGT TGG TGT GGT TGG (SEQ ID No. 1) and the 40-mer: ATC TCC GAT TGC CCC ACG ACG CAG TGG TCG GAG TTA CTT T (SEQ ID No. 2).

The proteins can be separated by means of the following methods:
I. isoelectric focusing
II. native polyacrylamide gel electrophoresis (PAGE)
III. native PAGE including 0.1% SDS.

Following this, the transfer onto the PVDF or nitrocellulose membrane takes place. The membranes are blocked by BSA and then incubated with fluorescently labelled aptamers.

To increase the detection specificity, the incubation with the specific aptamer can take place at higher temperatures (40° C., 45° C., 50° C.). The proteins are detected by way of fluorescent excitation at the fluorophore-specific wavelength.

The simultaneous detection of a plurality of target proteins (multiplex analysis) is enabled by: I. The use of a plurality of aptamers conjugated with different fluorophores. In parallel, the blot membranes are incubated with the various aptamers. II. The combination of the aptamer detection and the antibody detection. For example, the incubation of the aptamer can take place at room temperature in parallel to the incubation with the further antibody. If the aptamer is incubated e.g. at 40-60° C., the incubation with the antibody and the further antibody can be performed after the detection of the aptamer.

The three mentioned aspects allow for the fast and specific detection of several proteins in one test design. Thus, the established protocol for the aptamer blot clearly stands out from the test designs described so far.

Detailed Protocols:

The detection method comprises the following steps: step a) separation of the sample; step b) transfer of the separated sample onto a membrane; step c) contacting the membrane with an aptamer; step d) detection of the aptamer.

Provided that the separation in step a) was performed by means of isoelectric focusing (IEF), the developed protocol was carried out with the below materials and conditions as follows:

Step a): For the IEF, a gel having a pH gradient of pH 3-10 was used (BioRad). The samples were mixed with loading buffer (final concentrations: 2 mM lysin, 2 mM arginine, 5% glycerin) and applied onto the gel. An electric voltage was then applied to the gel and the respective running time was set (100V for 60 min; 250V for 60 min; 500V for 45 min). The cathode buffer contained 2 mM lysin and 2 mM arginine, the anode puffer 0.7 mM phosphoric acid.

Step b): A PVDF or nitrocellulose membrane was used as a blot membrane. The transfer onto the blot membrane was carried out at 10V for 60 min. The transfer buffer contained 0.7% acetic acid.

Subsequently, the membrane was blocked for 60 min at room temperature with 5% BSA in the respective selection buffer of the aptamer+0.1% TWEEN® (polysorbate).

Step c): The membrane was incubated with the aptamer for 60 min at room temperature or at 40° C., 45° C. or 50° C. For that purpose, 0.5-1.5 µg/ml aptamer was used in the respective selection buffer+0.1% TWEEN® (polysorbate)+1% BSA.

Step d): The detection was achieved by fluorescent excitation.

Provided that the polyacrylamide gel electrophoresis (PAGE) was applied for the separation in step a), the developed protocol was performed with the below materials and conditions as follows:

Step a): The PAGE can be carried out both under native and under denaturating conditions. A 10% polyacrylamide gel was used for the native PAGE (without SDS). The samples were mixed with loading buffer (31.25 mM TrisCl; pH 6.8+5% glycerin+bromphenol blue) and applied onto the gel. An electric voltage was then applied to the gel and the respective running time was set (100V for 60 min). A Tris/glycin buffer was used as a running buffer.

A small amount of SDS can be added to the native PAGE. Here, a 10% polyacrylamide gel was used. The sample containing 0.1% SDS (sample+31.25 mM TrisCl pH 6.8+5% glycerol+0.1% SDS+bromphenol blue) was applied onto this gel. An electric voltage was then applied to the gel and the respective running time was set (100V for 60 min). A Tris/glycin buffer including 0.1% SDS was used as a running buffer.

A 10% BisTris polyacrylamide gel was used for the denaturating PAGE. The denaturated sample was then applied onto this gel (sample buffer: 315 mM Tris pH 6.8, 10% SDS, 50 glycerin, 0.05% bromphenol blue, 25% β-mercaptoethanol). An electric voltage was then applied to the gel and the respective running time was set (200V for 30 min). A MOPS/Tris buffer including 5 mM EDTA, 1 mM sodium bisulfite and 0.1% SDS was used as a running buffer.

Step b): A PVDF or nitrocellulose membrane was used as a blot membrane. The transfer onto the blot membrane was carried out at 140 mA for 70 min. The transfer buffer contained 25 mM Tris, 192 mM glycine and 20% methanol.

Subsequently, the membrane was blocked for 60 min at room temperature with 5% BSA in the respective selection buffer of the aptamer+0.1% TWEEN® 20 (polysorbate 20).

Step c): The membrane was incubated with the aptamer for 60 min at room temperature or at 40° C., 45° C. or 50° C. For that purpose, 0.5-1.5 µg/ml aptamer was used in the respective selection buffer+0.1% TWEEN® 20 (polysorbate 20)+1% BSA.

Step d): The detection was achieved by means of a fluorescent excitation or ECL development.

The developed protocol also allows for the combination of the aptamer blot with the classic western blot. The incubation with the specific aptamer is performed prior to the treatment of the proteins with the primary and secondary antibodies, provided that the aptamer was incubated at higher temperatures (FIG. 1B). Had the membrane been incubated with the aptamer solution at room temperature, the membrane was initially incubated with the primary antibody and then in parallel with the aptamer and the secondary antibody. After that, the aptamer and the antibodies were detected in parallel.

The detection method comprises the following steps provided that the membrane was initially incubated with the aptamer and then with the antibodies: step a) separating the sample; step b) transferring the separated sample onto a membrane; step c) contacting the membrane with an aptamer; step d) detecting the aptamer, step i) contacting the membrane with the primary antibody, step ii) contacting the membrane with the secondary antibody, and detecting the antibody.

The developed protocol was performed with the below materials and conditions:

Step a): A 10% polyacrylamide gel was used. The sample containing 0.1% SDS was applied onto the gel (loading buffer: 31.25 mM TrisCl pH 6.8+5% glycerin+0.1% SDS+ bromphenol blue). An electric voltage was then applied to the gel and the respective running time was set (100V for 60 min). A Tris/glycin buffer including 0.1% SDS was used as a running buffer.

Step b): A PVDF or nitrocellulose membrane was used as a blot membrane. The transfer onto the blot membrane was carried out at 140 mA for 70 min. The transfer buffer contained 25 mM Tris, 192 mM glycine and 20% methanol.

Subsequently, the membrane was blocked for 60 min at room temperature with 5% BSA in the respective selection buffer of the aptamer+0.1% TWEEN® 20 (polysorbate 20).

Step c): The membrane was incubated with the aptamer for 60 min at temperatures ≥40° C. For that purpose, 0.5-1.5 µg/ml aptamer was used in the respective selection buffer+ 0.1% TWEEN® 20 (polysorbate 20)+1% BSA.

Step d): The detection was achieved by fluorescent excitation.

Step i): Incubation with the primary antibody at room temperature for 1 h or, as appropriate, overnight at 4° C.

Step ii): Incubation with the secondary antibody for 1 h at room temperature. The ECL method was used for detection.

The detection method comprises the following steps, provided that the membrane was initially incubated with the primary antibody and then in parallel with the secondary antibody and the aptamer: step a) separating the sample; step b) transferring the separated sample onto a membrane; step i) contacting the membrane with a primary antibody, step c) contacting the membrane with the aptamer and the secondary antibody; step d) or ii) detecting the antibody and the aptamer.

The developed protocol was performed with the below materials and conditions as follows:

Step a): A 10% polyacrylamide gel was used. The sample containing 0.1% SDS was applied onto the gel (loading buffer: 31.25 mM TrisCl pH 6.8+5% glycerol+0.1% SDS+ bromphenol blue). An electric voltage was then applied to the gel and the respective running time was set (100V for 60 min). A Tris/glycin buffer including 0.1% SDS was used as a running buffer.

Step b): A PVDF or nitrocellulose membrane was used as a blot membrane. The transfer onto the blot membrane was carried out at 140 mA for 70 min. The transfer buffer contained 25 mM Tris, 192 mM glycine and 20% methanol.

Subsequently, the membrane was blocked for 60 min at room temperature with 5% BSA in the respective selection buffer of the aptamer+0.1% TWEEN® 20 (polysorbate 20).

Step i): The incubation of the membrane with the primary antibody was performed at room temperature for 1 h or, as appropriate, overnight at 4° C.

Step c): The membrane was incubated with the aptamer and the secondary antibody at room temperature for 60 min. For this purpose, 0.5-1.5 µg/ml aptamer and a secondary antibody were used in the selection buffer of the aptamer+ 0.1% TWEEN® 20 (polysorbate 20)+1% BSA.

Step d or ii): The detection was achieved by fluorescent excitation or ECL development, respectively.

Example 1: Comparison Between Denaturating and Native PAGE and Isoelectric Focusing as a Separation Method for the Aptamer Blot (FIG. 2)

The interaction between aptamer and protein is both sequence-specific and structure-specific. Accordingly, native conditions should be of advantage to the separation of proteins for aptamer blot applications. A comparison was made between the aptamer-based detection of thrombin and streptavidin following the separation under native and denaturating conditions (FIG. 2).

Figure 2A:
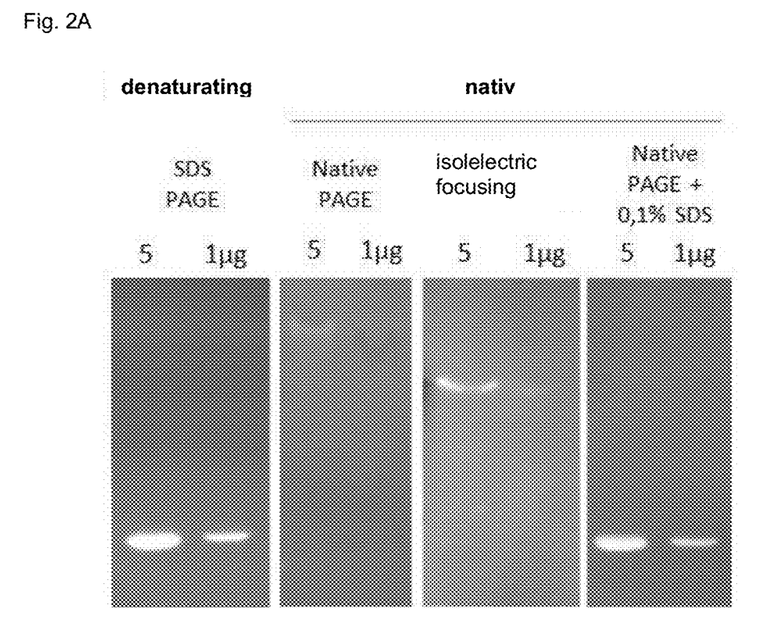
FIGS. 2A and 2B Detection of α-thrombin (FIG. 2A) and streptavidin (FIG. 2B) after separation under native conditions using specific aptamers. For comparison, α-thrombin and streptavidin were separated according to known protocols under denaturating conditions. The concentration of the FAM labelled aptamers was 1 µg/ml.
Figure 2B:
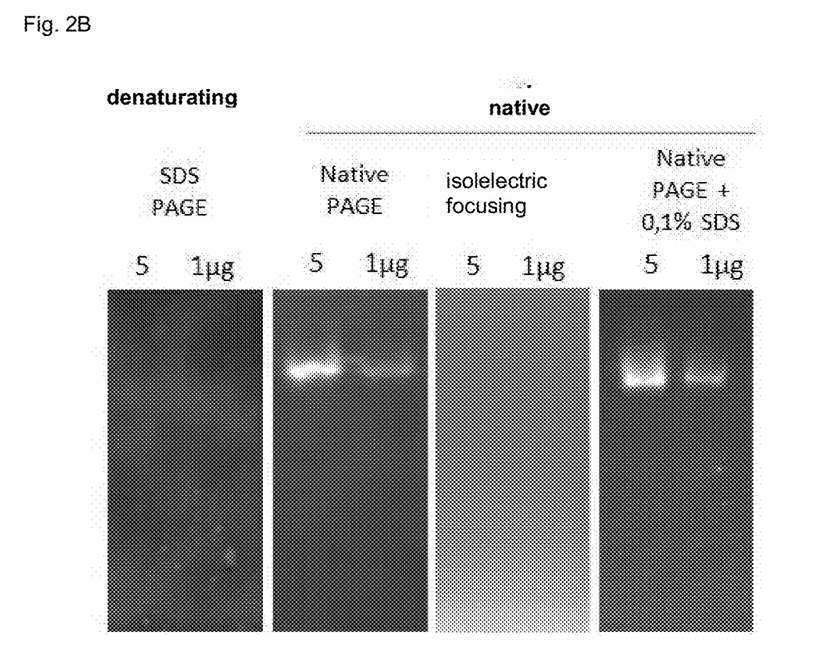

Literature has so far only reported on the separation of thrombin in the denaturating PAGE. As the aptamer blot works under these denaturating conditions, it can be assumed that the interaction between thrombin and the thrombin-binding aptamer (TBA) is exclusively based on sequence-specific interactions (FIG. 2A). However, the detection of streptavidin in the denaturating PAGE was not possible (FIG. 2B). It could be seen in Coomassie-dyed gels after the denaturating PAGE that the streptavidin was present in its monomeric form and the homotetrameric form of the native protein had been destroyed. Since streptavidin was not any longer detectable in its denaturated form it can be assumed that the interaction between streptavidin and its specific aptamer is based on structural interactions.

Thrombin was also analysed after a native PAGE in the aptamer blot (FIG. 2A). Compared to the denaturating PAGE, only very weak signals were detected, which also had a size of well over 100 kDa. This can supposedly be attributed to the formation of aggregates. The formation of the aggregates resulted in an aggravated inflow into the PAGE gel on the one hand, and in a very low transfer onto the PVDF membrane on the other. Streptavidin was also separated in a native PAGE and then analysed in the aptamer blot (FIG. 2B). Following the transfer of the protein onto PVDF membranes, the detection by means of the streptavidin-binding aptamer (SBA) was possible.

Furthermore, it was tested if isoelectric focusing (IEF) could be used for the aptamer blot. Both thrombin and streptavidin were applied onto IEF gels. Initially, the focusing was analysed using Coomassie dyes (data not shown). Both thrombin and streptavidin have flown into the IEF gels. Whereas thrombin was very well detectable in the aptamer blot (FIG. 2A), no bands could be detected with the SBA (FIG. 2B).

Another native separation method was analysed where the samples prior to the PAGE were denaturated neither by heat nor by reducing agents (FIGS. 2A and 2B, on the right). The loading and running buffer, however, was mixed with 0.1% SDS so that a uniform negative load of the proteins was achieved and the formation of aggregates was avoided. However, a denaturation of the proteins is not observed under these conditions. Clear signals were observed after the analysis of thrombin and streptavidin in the aptamer blot under these conditions. The streptavidin homotetramers were not destroyed by this treatment. Accordingly, this method seems to be most suitable for detecting proteins by the use of aptamer.

Example 2: Detection of Human α-Thrombin and Streptavidin in Protein Mixtures (FIG. 3)

Human α-thrombin was added to a HeLa cell extract while streptavidin was expressed as a fusion protein by means of the maltose-binding protein (MBP) in *E. coli*. The α-thrombin/HeLa mixture was separated in a denaturating SDS-PAGE, and the streptavidin/*E. coli* mixture was separated using a native PAGE.

Figure 3A:
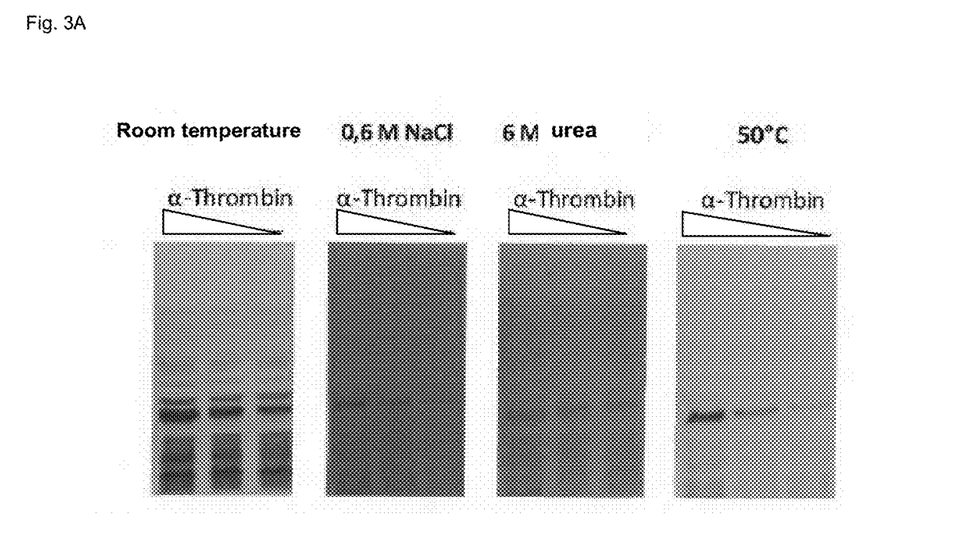

During the detection of α-thrombin it became clear that a number of HeLa proteins were detected in addition to α-thrombin (FIG. 3A, on the left). To reduce the number of unspecific bindings, several washing steps were performed following the aptamer incubation. On the one hand, the membranes were washed with 0.6M NaCl, and on the other hand with 6M urea. The unspecific bindings were reduced by each washing step, but the specific α-thrombin signal became weaker proportionally and the background became darker (FIG. 3A, centre). Accordingly, the two washing steps were not suited to increase the specificity in the aptamer blot.

Had the aptamer incubation, however, been performed at a temperature of 50° C., there was a strongly reduced background having only a slightly weaker α-thrombin signal (FIG. 3A, on the right).

Figure 3B:
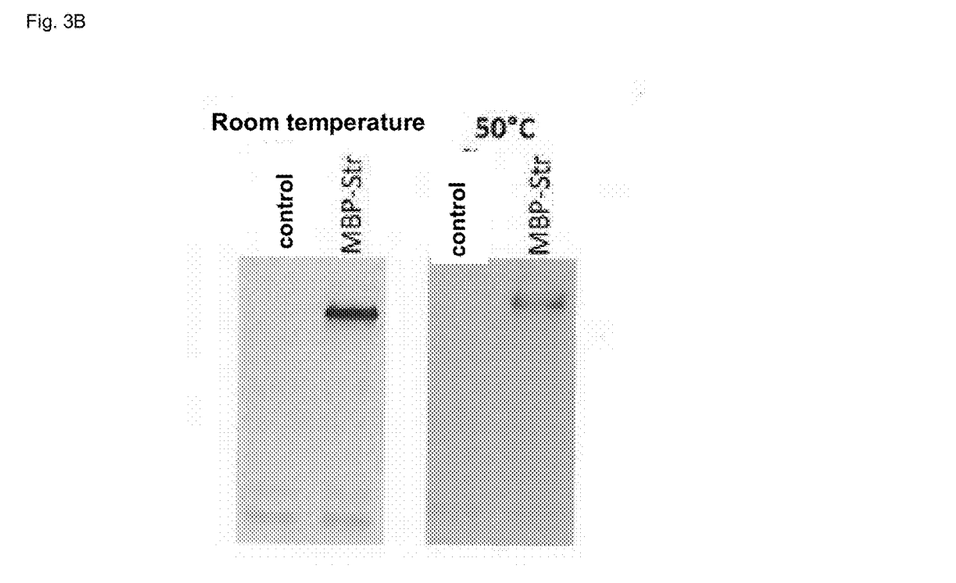

After a heterological expression and native PAGE of streptavidin in *E. coli*, significantly fewer unspecific bands than for α-thrombin were observed in the HeLa mixture (FIG. 3B, on the left). In order to increase the specificity of the detection, this membrane was also incubated with the streptavidin aptamer at 50° C. A reduction of unspecific bands was detectable (FIG. 3B, on the right-hand side).

Figure 3C:
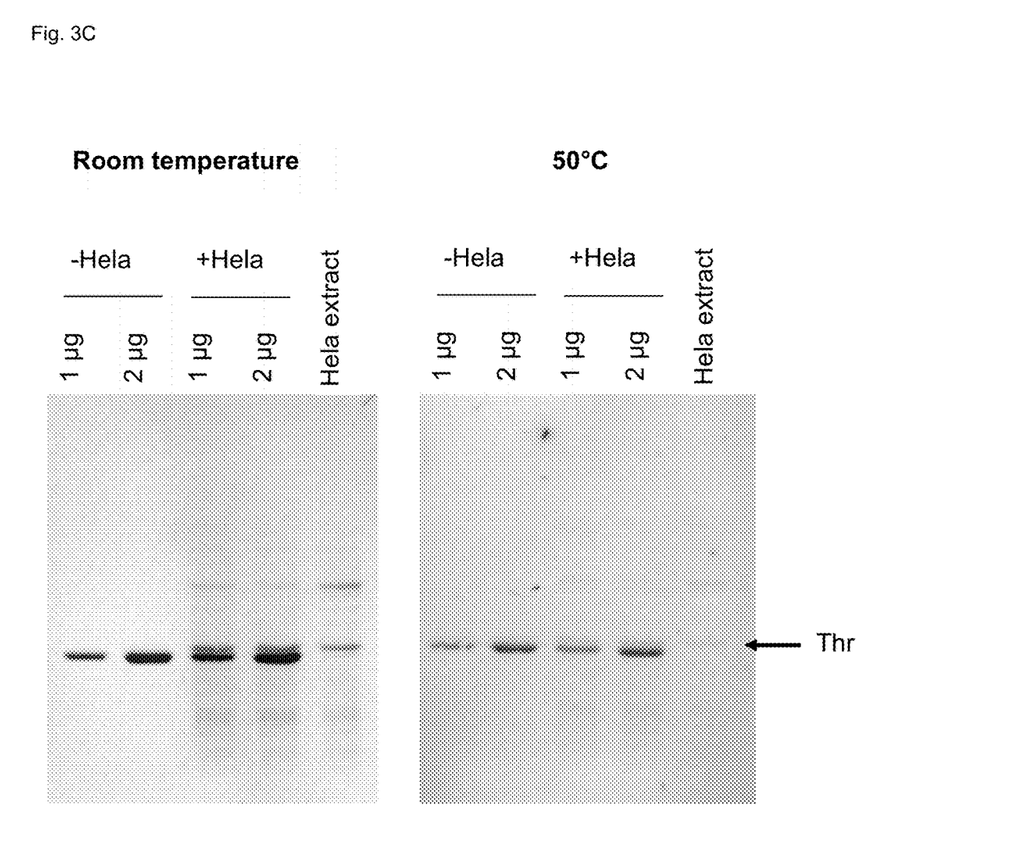
(FIG. 3C) and (FIG. 3D) 1 µg and 2 µg thrombin or streptavidin were mixed with HeLa extract, separated under native conditions including 0.1% SDS, and analysed by means of aptamer blot.
Figure 3D:
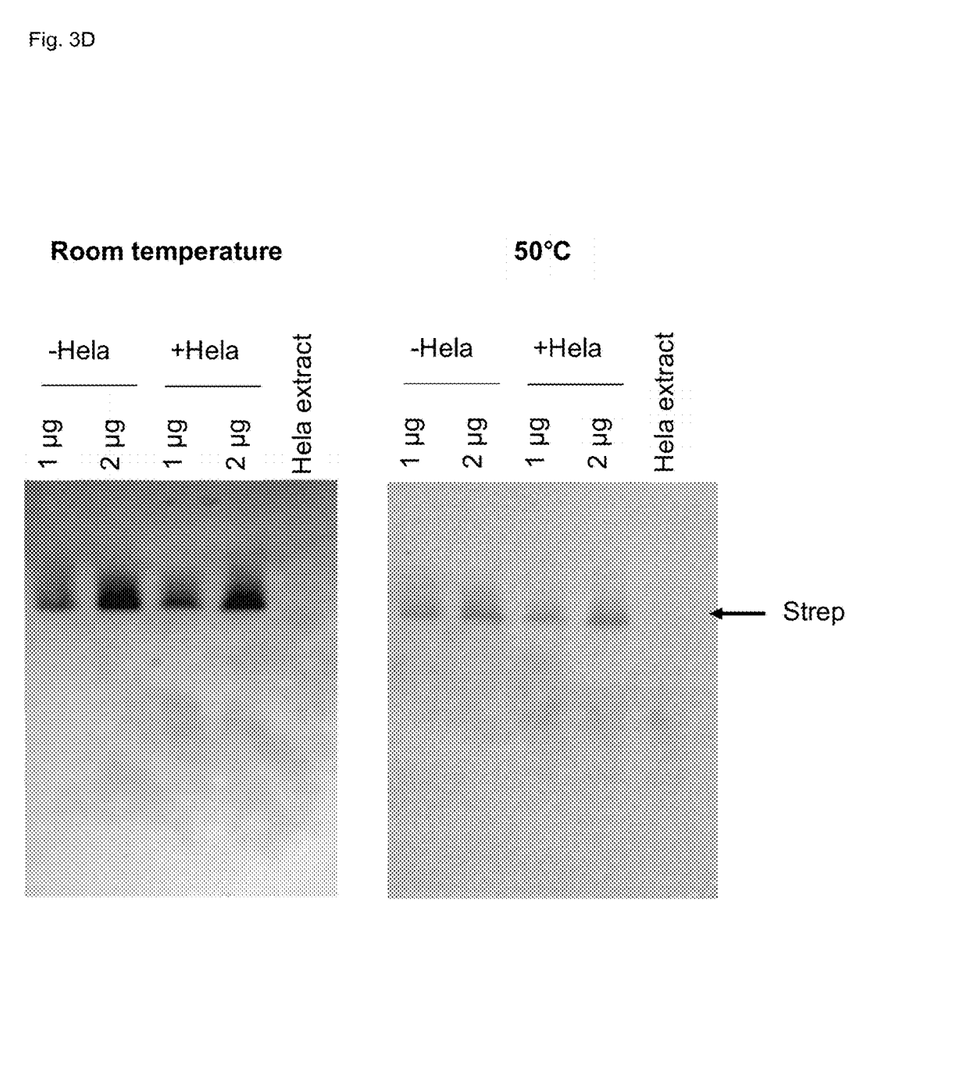

As it had become clear that a separation of human α-thrombin and streptavidin in native acrylamide gels and the use of 0.1% SDS yielded very good results in the aptamer blot, it was also analysed whether an incubation at higher temperatures leads to more specific results (FIGS. 3C and 3D). Consequently, thrombin or streptavidin were mixed with Hela extract and separated by means of native PAGE+ 0.1% SDS. The proteins were then transferred onto PVDF membranes; the membranes were blocked with BSA and incubated with TBA or SBA. While unspecific signals were observed with thrombin during the aptamer incubation at room temperature, the incubation at 50° C. allowed for a much more specific detection of thrombin (FIG. 3C). The incubation with the streptavidin-binding aptamer did neither produce any unspecific signals at room temperature nor at 50° C. (FIG. 3D). SBA seems to be much more specific than TBA.

Example 3: Combination of Aptamer and Western Blot (FIG. 4)

As considerably more antibodies than aptamers have been available for the detection of proteins until now, the compatibility of western and aptamer blot was analysed. To this end, both human α-thrombin and streptavidin were mixed with Hela extract and then actin was tested by means of western blot, and thrombin by means of the aptamer blot.

The protein mixtures were separated in a native PAGE with 0.1%. Next, the proteins were transferred onto a PVDF blot membrane, and the membrane was blocked using BSA. The membrane was then incubated with the primary antibody against actin overnight. This was followed by the incubation of the membrane at room temperature with the TBA or SBA and a secondary antibody conjugated with the horseradish peroxidase. Finally, the aptamer and the secondary antibody were detected in parallel.

Figure 4A:
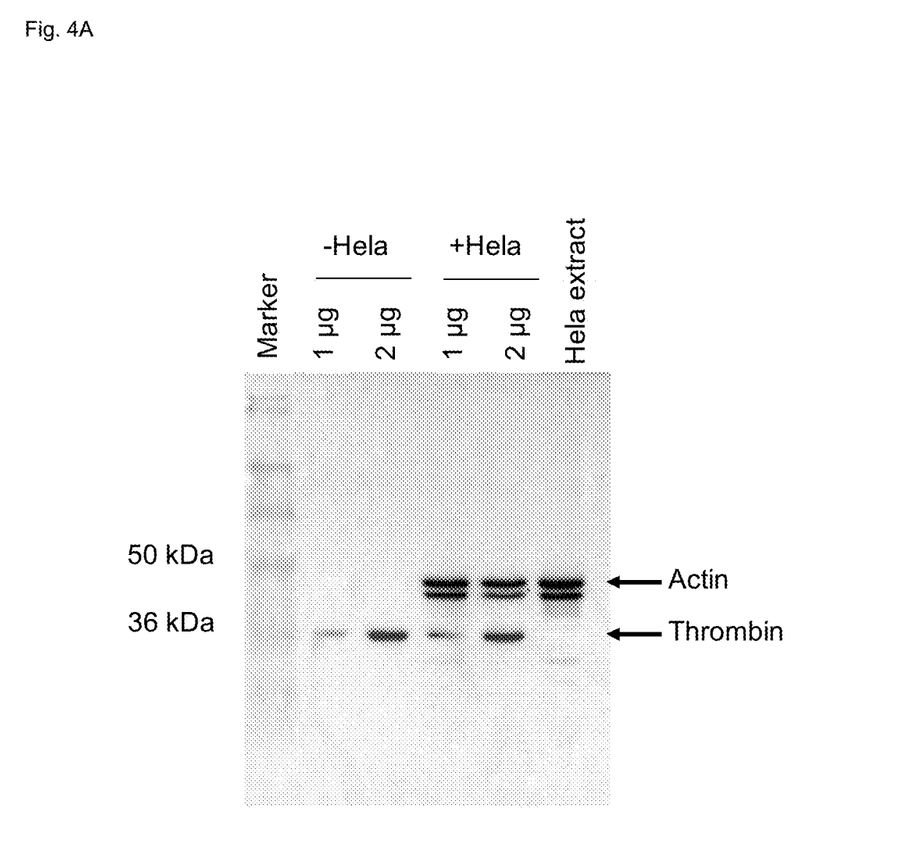
FIGS. 4A and 4B Combination of western and aptamer blot. Human α-thrombin (FIG. 4A) and streptavidin (FIG. 4B) were mixed with HeLa extract and separated in a native PAGE including 0.1% SDS. After the transfer of proteins onto a membrane and the blocking of the membrane, the incubation with the primary antibody against actin was carried out. The membrane was then treated with the aptamer and the horseradish peroxidase-labelled secondary antibody at room temperature.
Figure 4B:
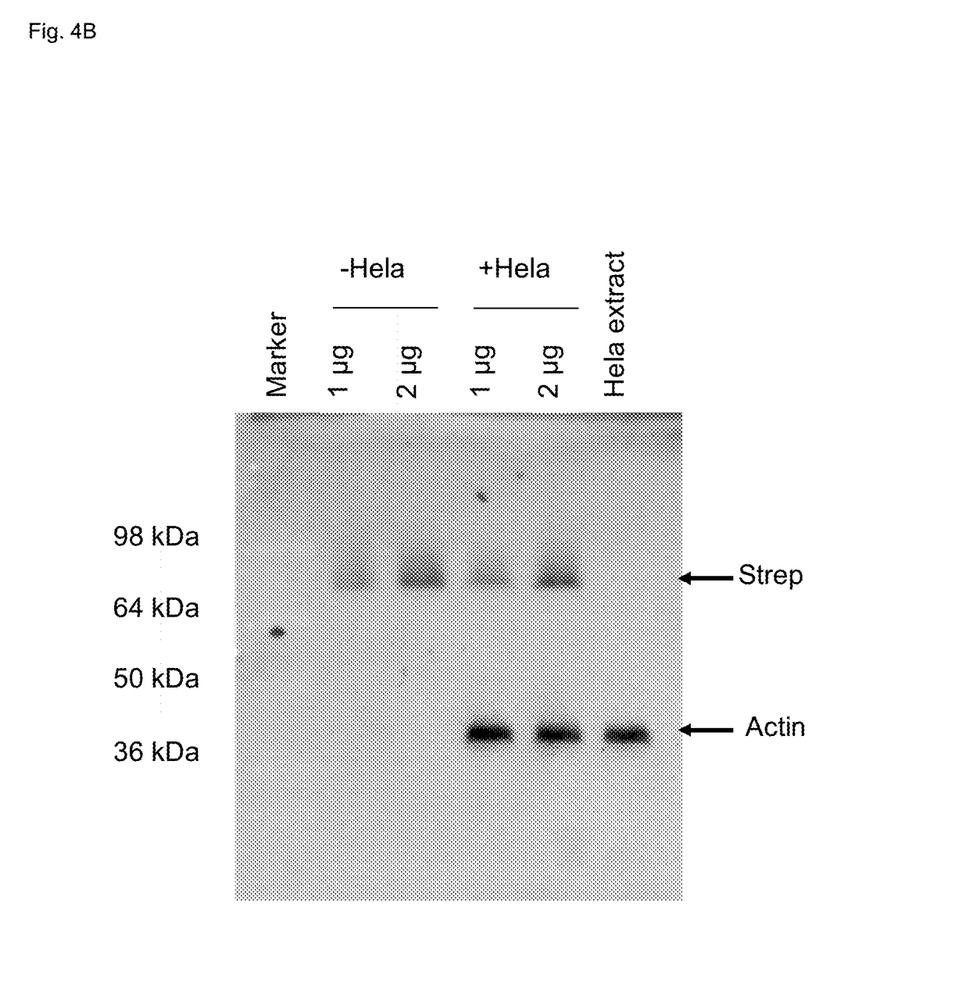

This test design made it possible to detect both thrombin and streptavidin jointly with actin (FIG. 4). In the tests without thrombin or streptavidin, no signals were detected in the corresponding molecular weight range. The successful combination of western and aptamer blot could thus be demonstrated.

Figure 5:
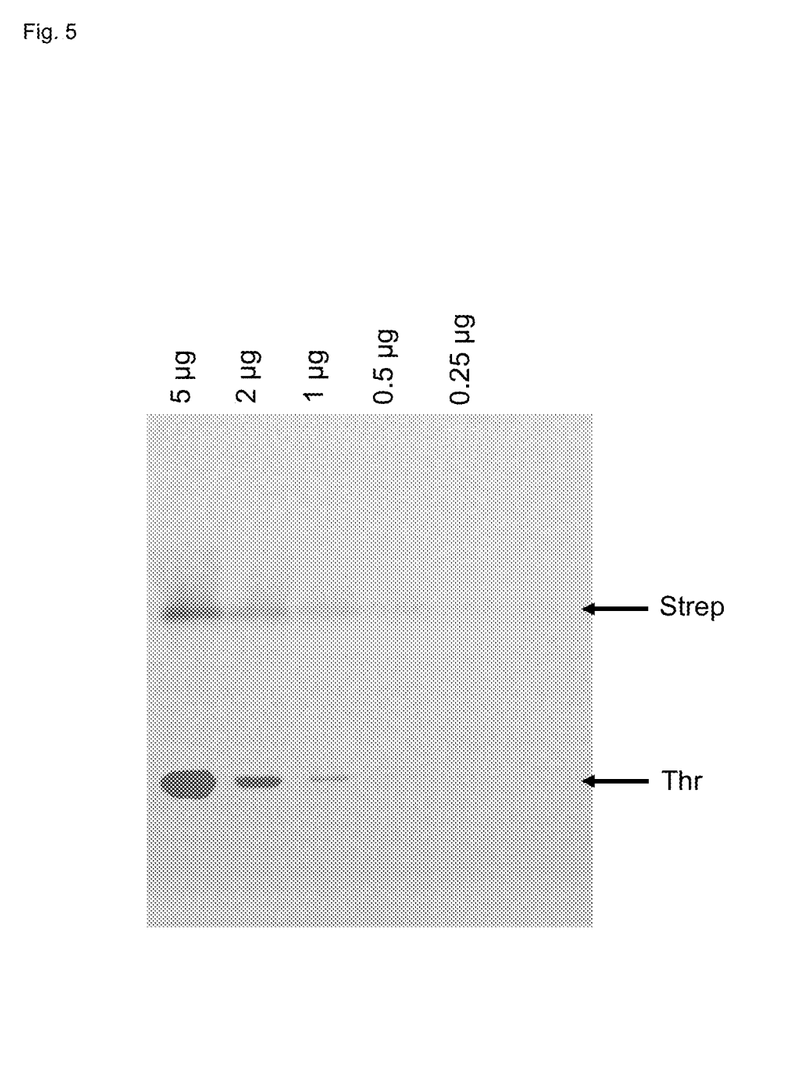
FIG. 5 Multiplex detection of thrombin and streptavidin in the aptamer blot. Thrombin was mixed with streptavidin. The protein mixture was separated in a native PAGE with 0.1% SDS. The concentration of the each aptamer amounted to 1 µg/ml. Trace 1: 5 µg thrombin/streptavidin each; trace 2: 2 µg thrombin/streptavidin each; trace 3: 1 µg thrombin/streptavidin each; trace 4: 0.5 µg thrombin/streptavidin each; trace 5: 0.25 µg thrombin/streptavidin each.

Example 4: Multiplex Detection of Thrombin and Streptavidin (FIG. 5)

The use of fluorescently labelled aptamers enables the parallel detection of a plurality of proteins in one test. The feasibility was shown by way of example for a thrombin-streptavidin mixture (FIG. 5). The TBA was labelled using Cy5 and the SBA using FAM. The protein mixture was separated in the native PAGE including 0.1% SDS. Clear signals were observed both for thrombin and for streptavidin following the transfer of proteins onto PVDF membranes and the joint incubation with both aptamers. The limit of detection for streptavidin was 0.25 µg and for thrombin 0.5 µg.

Example 5: Comparison Between Native and Denaturating Separation Methods Using the Native SDS-PAGE (FIG. 6)

Figure 6:
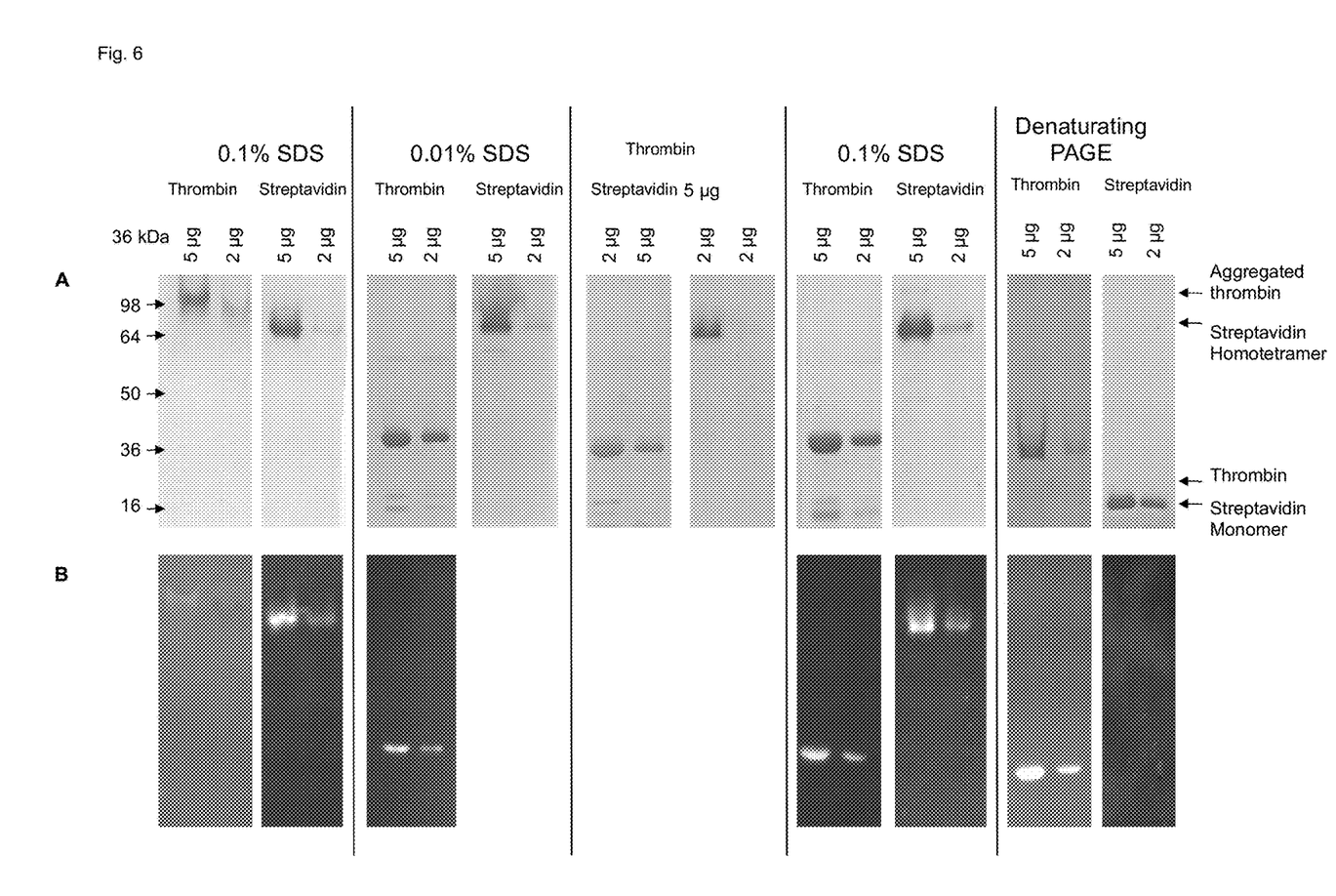
FIG. 6 Comparison between native and denaturating gel electrophoresis of thrombin and streptavidin and the native SDS-PAGE. In the native SDS-PAGE, various SDS quantities (0.01%; 0.05%; 0.1%) were analysed in the loading and running buffer. (A) Coomassie-dyed polyacrylamide gels; (B) aptamer blot.

Comparing the running behaviour of thrombin in polyacrylamide gels after Coomassie staining you find thrombin to form aggregates under native conditions (FIG. 6A). The formation of aggregates results in very weak signals in the aptamer blot (FIG. 6B). The addition of even small quantities of SDS (starting from 0.01% SDS) to the loading and running buffer during the gel electrophoresis prevents the formation of aggregates. The thrombin detection thus becomes much more sensitive, and it can be assumed that the native structure of thrombin is preserved.

Streptavidin is present as a native, functional protein in its homotetrameric form. This homotetrameric structure is also very well detectable in Coomassie-dyed polyacrylamide gels. Under native conditions and following the addition of 0.01%, 0.05% or 0.1% SDS to the loading and running buffer, one could see that streptavidin as a native protein had flown into the gels because the protein in reference to a marker was detected at a size of approx. 64 kDa (FIG. 6A). Under denaturating conditions, only the streptavidin monomers were visible in the gel. As a result, the streptavidin detection was not possible in the aptamer blot under denaturating conditions (FIG. 6B). The detection of streptavidin in the aptamer blot, however, was possible in the native PAGE or native SDS-PAGE including 0.1%.

The invention claimed is:

1. A method for the in vitro detection of a first protein in a sample, comprising the steps of:
   a) separating the sample by means of a native separation method;
   b) transferring the separated sample onto a membrane;
   c) contacting the membrane with an aptamer which specifically binds to the first protein, wherein the contacting is performed at a temperature of ≥30° C., and
   d) detecting the first protein by detecting the aptamer bound to the first protein.

2. The method according to claim 1, wherein the native separation method is an electrophoretic separation.

3. The method according to claim 1, wherein in the native separation method, a sodium dodecyl sulfate (SDS) concentration of 0% to 0.2% SDS is used.

4. The method according to claim 1, wherein the contacting of the membrane with the aptamer in step c) is performed at a temperature of 30° C. to 70° C.

5. The method according to claim 1, wherein the sample is a protein-containing mixture.

6. The method according to claim 1, wherein the sample is a protein-containing mixture obtained from a cell culture suspension, a cell culture supernatant, a tissue sample or a body fluid, or comprises a cell culture suspension, a cell culture supernatant, a tissue sample or a body fluid.

7. The method according to claim 1, wherein the aptamer includes a modification selected from the group consisting of: a biotin labelling, fluorescent labelling, radioisotope labelling, digoxigenin labelling, peroxidase labelling, alkaline phosphatase labelling, and a labelling using nanoparticles.

8. The method according to claim 1, wherein the detection of the aptamer is direct or indirect.

9. The method according to claim 1, wherein the detection of the aptamer is performed by means of an enzymatic, auto-radiographic or fluorescent detection method.

10. The method according to claim 1, wherein the detection of the aptamer is indirect and the indirect detection of the aptamer uses an aptamer-specific antibody bound to the aptamer.

11. The method according to claim 1, wherein an aptamer-specific antibody is used for the detection of the aptamer and the aptamer-specific antibody includes a modification selected from the group consisting of: a biotin labelling, fluorescent labelling, radioisotope labelling, digoxigenin labelling, peroxidase labelling, alkaline phosphatase labelling, and a labelling using nanoparticles.

12. The method according to claim 1 for the additional detection of a second protein in the sample, comprising additional steps:
   i. following step b), the membrane is contacted with a binding molecule which specifically binds to the second protein; and
   ii. the second protein is detected through detection of the binding molecule bound to the second protein.

13. The method according to claim 1 for additional detection of a second protein in the sample, comprising the additional steps:
   i. following step b), the membrane is contacted with a binding molecule which specifically binds to the second protein; and
   ii. the second protein is detected through detection of the binding molecule bound to the second protein;
   wherein the binding molecule includes a modification selected from the group consisting of: a biotin labelling, fluorescent labelling, radioisotope labelling, digoxigenin labelling, peroxidase labelling, alkaline phosphatase labelling, and a labelling using nanoparticles.

14. The method according to claim 1 for additional detection of a second protein in the sample, comprising additional steps:
   i. following step b), the membrane is contacted with a binding molecule which specifically binds to the second protein; and
   ii. the second protein is detected through detection of the binding molecule bound to the second protein;
   wherein the binding molecule is a further aptamer or an antibody.

15. The method according to claim 2, wherein the native separation method is gel electrophoresis.

* * * * *

SEQUENCE LISTING

<160> NUMBER OF SEQ ID NOS: 2

<210> SEQ ID NO 1
<211> LENGTH: 15
<212> TYPE: DNA
<213> ORGANISM: Artificial Sequence
<220> FEATURE:
<223> OTHER INFORMATION: Thrombin-bindendes Aptamer

<400> SEQUENCE: 1
ggttggtgtg gttgg                                                    15

<210> SEQ ID NO 2
<211> LENGTH: 40
<212> TYPE: DNA
<213> ORGANISM: Artificial Sequence
<220> FEATURE:
<223> OTHER INFORMATION: Streptavidin-bindendes Aptamer

<400> SEQUENCE: 2
atctccgatt gccccacgac gcagtggtcg gagttacttt                         40